United States Patent [19]

Dayton

[11] Patent Number: 5,344,451
[45] Date of Patent: Sep. 6, 1994

[54] SYNTHETIC RECONSTRUCTIVE IMPLANT DEVICE

[76] Inventor: Michael P. Dayton, 14802 Hadleigh Way, Tampa, Fla. 33624

[21] Appl. No.: 59,178

[22] Filed: May 5, 1993

Related U.S. Application Data

[63] Continuation of Ser. No. 903,502, Jun. 24, 1992, abandoned.

[51] Int. Cl.$^5$ .............................................. A61F 2/12
[52] U.S. Cl. ........................................... 23/8; 623/7; 623/11
[58] Field of Search .................... 623/7, 8, 11, 17, 1

[56] References Cited

U.S. PATENT DOCUMENTS

| | | | |
|---|---|---|---|
| 4,904,260 | 2/1990 | Ray et al. | 623/17 |
| 5,019,096 | 5/1991 | Fox, Jr. et al. | 623/11 |
| 5,092,882 | 3/1992 | Lynn et al. | 623/8 |

FOREIGN PATENT DOCUMENTS

| | | | |
|---|---|---|---|
| 2164343 | 3/1986 | United Kingdom | 623/8 |

*Primary Examiner*—David Isabella
*Assistant Examiner*—Debra S. Brittingham
*Attorney, Agent, or Firm*—Eugene E. Renz, Jr.

[57] ABSTRACT

A synthetic reconstructive surgical implant device and method for making the same in which the device is suitable for implanting in a human. The device includes a sealed prosthesis envelope having a predetermined shape when filled, with the envelope being formed from an elastic polymer having a microporous structure with a texturized or non-texturized surface, such as silicone, polyurethane, polyvinylalcohol polyethylene, polyesters, hydrogels, tetrafluroethylene and polytetrafluroethylene, fluorosilicone and mixtures thereof. The envelope is filled with a biocompatible viscoelastic material in an amount sufficient to provide the predetermined shape. The biocompatible viscoelastic material is a sterile, non-pyrogenic solution which, in a preferred embodiment may be selected from salts of chondrotin sulfate, salts of hyaluronate, hydroxyproplymethylcellulose and mixtures thereof. In another preferred embodiment, the device includes a bioactive substance admixed in the polymer for elution from the microporous structure of the envelope after implantation. The bioactive substance may be selected from the group of heparin, prostacyclenes, steroids, ibuprofen, antimicrobials, antibiotics, tissue plasma activators, monoclonal antibodies, snake venom protein by-products, antifibrosis agents, cyclosporine and mixtures thereof. The rate of elution of the bioactive substance is controlled by selecting a pore size for the microporous structure in response to the concentration and molecular weight of the bioactive substance to achieve equilibrium between the envelope surface and the tissue proximate the envelope upon implant.

3 Claims, No Drawings

SYNTHETIC RECONSTRUCTIVE IMPLANT DEVICE

This is a continuation of copending application Ser. No. 07/903,502 filed on Jun. 24, 1992, now abandoned.

FIELD OF THE INVENTION

The present invention relates to an improved reconstructive surgical implant device, and more particularly to a device useful as a prosthesis and a method for making the same which is biocompatible, natural in appearance and feel, and which is adapted to resist problems from fibrotic capsular contracture and/or post implant infection. The present invention also relates to a new procedure in which bioactive substances may be used.

BACKGROUND OF THE INVENTION

In recent years, the use of reconstructive surgical implant devices has become a commonly elected surgical procedure. In some instances, the procedure is done to correct the patient's appearance for cosmetic reasons. More important, of course, is the use of this procedure to restore the patient to an appearance that approximates that which existed before other surgery or injury. One major use is, of course. postmastectomy breast reconstruction. At the same time, as the procedure is more common, some of the disadvantages of the procedure are causing more concern.

At the present time, there are three major types of mammary prostheses in use. These prostheses procedures include the autologous breast prosthesis, which is fashioned by grafting the patient's own abdominal fatty tissues, which are, of course, not synthetic. This procedure has the advantages of having a natural appearance and feel, and is completely biocompatible. Unfortunately, it is about three tinges as expensive as synthetic procedures, in part because of the need for two procedures. In addition, this procedure is a more involved surgical procedure with all of the attendant risks which that brings.

A second method or procedure currently employed is the use of a silicone envelope which has been filled with synthetic saline solution. This procedure is much less expensive than the first procedure and also offers appropriate biocompatibility of the filler. However, the use of a saline solution filled silicone envelope gives an unnatural appearance and feel. More important, perhaps, is the fact that the envelope is prone to capsular contracture or infection. For these reasons, this procedure is not truly acceptable and is to be avoided when an alternative procedure becomes available.

The third presently available method is the use of a silicone envelope which has been filled with synthetic silicone gel. This method is also relatively inexpensive like the second method, but has the additional advantage of providing a relatively good appearance and feel. This is the most popular procedure currently in use. However, this method also has some aspects which give rise to a concern. The filler is, potentially at least, a non-biocompatible filler and may even cause more problems, although studies are not at all complete in this area. Nevertheless, the envelope is also prone to capsular contracture or infection and is not totally acceptable for all persons under all circumstances.

Some improvements have been suggested in these methods. One suggestion is disclosed in U.S. Pat. No. 5,092,882, where a multiple compartment breast prosthesis is shown. In this patent, three separate compartments are filled with a conventional silicone gel. The separation of the compartments provides a better profile for the prosthesis. However, no suggestions are contained in this patent which would overcome the above described deficiencies with respect to the use of a non-biocompatible filler. Also, as previously noted, the envelope is prone to capsular contracture and/or infection.

Appearance is of primary concern, although not to the detriment of the health of the patient. U.S. Pat.No. 5,022,942 discloses a surgical prosthesis which has a textured exterior surface which has been formed from non-absorbent material which is substantially free from pores and interstices. Several methods of manufacturing the device are disclosed. Infection is stated to be avoided or reduced because the silicone rubber is non-absorbent to body fluids. This does not, however, change the concern which has been expressed above with respect to envelope compatibility with the human body.

Mother concern which the prior art has addressed is described in U.S. Pat. No. 5,026,394. In this reference, a reinforcement member is provided which is suggested to prevent or reduce capsular contracture due to scar tissue formation after implantation, resulting in maintenance of the desired profile and softness of the in, planted prosthesis. However, again there is no consideration of avoiding the problems described above which are caused by the use of conventional materials.

One patent which has offered a suggested filler material which has certain advantages over silicone oil is U.S. Pat. No. 5,067,965. In this patent, the use of certain salts of polyvinylpyrollidone is suggested because of its approximation of the x-ray absorption of normal breast tissue. The polymer is said to be bio-compatible. However, use of the polymer requires what appears to be close adjustment of the molecular weight, partly to adjust the x-ray or radio density properties, and partly to improve compatibility. It is noted that the reference explicitly teaches that the vast majority of the combinations suggested are completely excretable by the body and present no danger of foreign body reaction. The concern remaining is for the rest of the suggested combinations, and particularly those of higher molecular weight.

Accordingly, it is an object of the present invention to provide a reconstructive surgical in, plant device which avoids the use of a non-biocompatible filler and which employs an envelope which is not prone to capsular contracture and/or infection.

Mother object of this invention is to provide a device and method for its use as a reconstructive surgical implant device in which the envelope achieves compatibility with the patient.

Yet another object of the present invention is to provide a device which employs materials of construction which are free from the problems of silicone gels and other potentially non-biocompatible fillers, while not introducing concern for foreign body reaction and inability of tile body to remove the material.

Other objects will appear hereinafter.

SUMMARY OF THE INVENTION

It has now been discovered that the above and other objects of the present invention may be accomplished in the following manner. Specifically, the present invention provides a reconstructive surgical implant device suitable for implanting in a human, and the method of making such a device. Applications of the device of this invention include breast implants, inflatable breast implants, tissue expanders both temporary and permanent, pectoral implants chin prosthesis and testicular implants.

The device includes a sealed prosthesis envelope having a predetermined shape when filled. The envelope is formed from an elastic polymer having a microporous structure. Preferred polymers are polymers selected from silicone, polyurethane, polyvinylalcohol, polyethylene, polyesters, tetrafluroethylene and polytetrafluroethylene, hydrogels fluorosilicone and mixtures thereof.

The outer surface of the envelope may be texturized or non-texturized. The inside of the sealed prosthesis envelope is filled with a biocompatible viscoelastic material, in an amount sufficient to provide the predetermined desired shape. Preferred examples of the biocompatible viscoelastic material are sterile, non-pyrogenic solutions such as salts of chondrotin sulfate, salts of hyaluronate, naturally occurring polysaccharides, hydroxyproplymethylcellulose and mixtures thereof.

In a preferred embodiment, the device includes a bioactive substance admixed in the polymer to permit elution through the microporous structure of the envelope after implantation of the device in a patient. Preferred bioactive substances are selected from heparin, prostacyclenes, steroids, ibuprofen, antimicrobials, antibiotics, tissue plasma activators. monoclonal antibodies, snake venom protein by-products, antifibrosis agents, cyclosporine and mixtures thereof. Any bioactive substance of need to the patient may be used in the manner described herein.

It is important to control the rate of elution of the bioactive substance and this is done by selecting a pore size for the microporous structure of the envelope polymer to cooperatively respond to the concentration and molecular weight of said bioactive substance to achieve a desired equilibrium between the envelope surface and the tissue proximate said envelope upon implant.

DETAILED DESCRIPTION OF THE PREFERRED EMBODIMENT

As set forth above, the present invention in its simplest embodiment comprises a reconstructive surgical implant device suitable for implanting in a human. Applications of the device of this invention include breast implants, inflatable breast implants, tissue expanders both temporary and permanent, pectoral implants chin prosthesis and testicular implants. The two primary components of the device are the sealed prosthesis envelope with a microporous structure and the biocompatible viscoelastic material filling the envelope. The third component, a bioactive substance, preferably is included for elution from said microporous structure of said envelope after implantation.

Turning first to the sealed prosthesis envelope, it is contemplated that conventional implant polymers be used. It is important to have a microporous structure such as is produced by silicone elastomers which are vulcanized or cured at ambient or elevated temperatures. It is useful also to consider other polymers such as polyurethane, polyvinylalcohol, polyethylene, polyesters, tetrafluroethylene and polytetrafluroethylene, hydrogels fluorosilicone, and mixtures thereof with or without the silicone elastomer. Other polymers and elastomers which form a microporous structure when cured may also be employed in the present invention.

It is intended that the envelope consist of a cured or solid form of the polymer, shaped into a pouch or envelope which is consistent in the size and shape of the prosthesis size and shape. The outer surface may possess a texturized outer surface to further diffuse the biological fibrotic capsular response to the implant. Conventional technique is capable of doing this at the present time. In one manufacturing technique, a circular hole is left in the rear of the envelope which permits removal of the cured pouch from the prosthesis mold. This hole, if it exists, must be sealed or patched with a second piece of the cured polymer. Once the envelope is cured and sealed, it is ready to receive the viscoelastic material.

The purpose of the viscoelastic material is to provide a safe material which provides tile appearance and feel most closely resembling nature. Such a goal has not been achieved using conventional gel fillers. It is also desirable that the gels of the present invention be relatively inexpensive and that they be of a substance which has been proven to be biocompatible to the extent that is possible.

Preferred viscoelastic materials include cross-linked and uncross-linked forms of carbohydrate hyaluron, sodium hyaluronic acid, sodium chondrotin mixed with sodium hyaluronic acid, methylcellulose, polysaccharides,· hydroxypropylmethylcellulose, polyacrylamide and other synthetic and or natural gels which exhibit a viscoelastic property. These materials have been approved by the Food and Drug Administration as being clinically safe and effective for use in ophthalmic, orthopedic and/or urological procedures. The term "viscoelastic" is intended to include those materials which are biocompatible gels possessing a viscosity similar to that of silicone gel, but whose physical properties can be varied by adjusting the density, molecular weight and degree of crosslinking of the ingredients to provide a specific match for the polymer envelope selected, to thereby provide the end results desired.

Several products are currently on the market which are suitable viscoelastic materials for use as fillers in the present invention. Occucoat ® ophthalmic surgical aid, manufactured by Storz Ophthalmics, Inc., is a sterile, isotonic, nonpyrogenic viscoelastic solution of highly purified, noninflamitory 2% hydroxyproplymethylcellulose with a molecular weight greater than 80,000 daltons. It has been designed for use as an ophthalmic surgical aid in anterior segment surgical procedures including, for example, cataract extraction and intraocular lens implantation. It is injected, using a cannula, into the anterior chamber of the eye to provide protection to the corneal endothelium. It is noted for its ability to help the vitreous face of the eye to be pushed back due to its viscoelasticity, thus preventing formation of a postoperative fiat chamber.

Viscoat ® sterile ophthalmic vicsoelastic solution is a sterile, non-pyrogenic, viscoelastic solution of a highly purified, non-inflammatory medium molecular weight fraction of sodium chondroitin and sodium hyaluronate. Viscoat ® solution is noted for protecting the corneal endothelium and other ocular tissues during anterior segment surgeries. The molecular weight of the chondroitin fraction is about 22,500 daltons, while the sodium hyaluronate molecular weight is about 500,000 daltons.

Vitrax ® solution is a sterile, non-pyrogenic, viscoelastic solution of sodium hyaluronate in a highly purified form and which is non-inflammatory as well. This solution is used in glaucoma filtration surgery. Similarly, Healon ® solution is sterile, non-pyrogenic, and viscoelastic, in this case being formed from a highly purified, non-inflammatory, high molecular weight fraction of sodium hyaluronate dissolved in physiological sodium chloride phosphate buffer. It also is known for its value in ophthalmic treatments.

A specific device for making a breast prosthesis employed Dow Corning Silastic MDXr/4515, Q7-2245 and Q7-2213 polymers. The polymer is mixed in a 3 to 1 ratio with ethyl ether to form a solution suitable for coating a prosthesis mold. The polymer is then vulcanized and removed from the mold in the form of a pouch consistent in size and shape to the size and shape of the prosthesis which is desired, and may posses a texturized outer surface to further diffuse the biological fibrotic capsular response to the implant. Often but not always, a circular hole in the rear of the envelope permits the removal of the cured pouch from the prosthesis mold. This hole must be sealed or patched with a second piece of the cured polymer. Upon completion of the seal, the envelope is injected with sufficient volume of the viscoelastic solution to achieve the predetermined size and shape.

The prosthesis is now ready to be used. The envelope is porous and sturdy, and is easily implanted using conventional techniques. The use of the viscoelastic solution to fill the envelope imparts a natural shape and size to the prosthesis. This is due to the viscoelastic nature of these solutions or gels, which are very similar to the silicone gels which imitate natural tissue without any of the disadvantages of potential bio-incompatibility or change over time to less appropriate hardness or stiffness. In addition, the compatibility of the viscoelastic solutions, all of which are sufficiently biocompatible for use in the interior portion of the eye, provides no deleterious effects on the mammary tissue surrounding the implant. All of these viscoelastic solutions are suited for introduction into the envelope via a syringe or cannula. It can be appreciated that solutions which can be inserted into the anterior portion of the eye can readily by inserted into the envelope.

However, in order to further improve the efficacy of the present invention, it is often desirable to add an additional ingredient in the form of a bioactive substance. These bioactive substances elute through the microporous structure of the envelope after implantation of the device in a patient.

Preferred bioactive substances are heparin, prostacyclenes, steroids, ibuprofen, antimicrobials, antibiotics, tissue plasma activators, monoclonal antibodies, snake venom protein by-products, antifibrosis agents, cyclosporine and mixtures thereof. Of course, virtually any bioactive substance of need to the patient is a possible agent for treating the patient, depending upon the needs of the treatment.

Once again, a specific device is made using Dow Corning Silastic Q7-2245 polymer. A bioactive substance is incorporated into the polymer prior to vulcanization so that the substance is absorbed by the patient through the micropores of the polymer. This method permits the envelope to be constructed from a monolayer or from multiple layers of the polymer.

Use of an outer layer with none of the bioactive substance incorporated in it will reduce the likelihood of a burst release phenomenon, which is also described as a large, uncontrolled, uneven release of the bioactive substance into surrounding tissue. In this embodiment, a layer of untreated polymer is formed on each side of a layer which has a bioactive substance entrapped in the polymer matrix prior to migration outward through the micropores.

Alternatively, the completed cured polymer envelope may be submerged in a solution of the bioactive substance. Variables determining the rate and volume of the bioactive substance which is taken up or absorbed into the polymer are time, concentration and temperature. Any desired concentration can be achieved.

The dynamics of polymer matrix release depends on the equilibrium between the surrounding tissues and the prosthesis surface where the bioactive substance releases from the microporous polymer. The rate of elution of the bioactive substance is controlled by selecting a pore size for the microporous structure of the envelope polymer so that it will cooperatively respond to the concentration and molecular weight of said bioactive substance. This permits the device to achieve a desired equilibrium between the envelope surface and the tissue proximate the envelope after it has been implanted.

The concentration of tile bioactive substance which has been added to the polymer, along with the pore size of the polymer and the molecular weight of each molecule of the bioactive substance all interact together with the external milieu in a dynamic equilibrium to provide a localized, non-systemic, prophylactic effect.

As a result of the present invention, a synthetic reconstructive surgical implant device of this invention results in a prosthesis which would contain a proven biocompatible and naturally looking/feeling gel. The gel is contained within an envelope which will resist or eliminate the problem of capsular contracture and also eliminate post-implant infection. Applications of the device of this invention include but are not limited to procedures for breast implants, inflatable breast implants, tissue expanders both temporary and permanent, pectoral implants chin prosthesis and testicular implants.

While particular embodiments of the present invention have been illustrated and described, it is not intended to limit the invention, except as defined by the following claims.

I claim:

1. A synthetic reconstructive surgical breast implant device suitable for implanting as a breast implant in contact with tissue in a human comprising:

a sealed envelope having a surface exposed for direct contact with said tissue, said envelope having a predetermined shape when filled, said enveloped being formed from an elastic polymer having a microporous structure of a selected pore size;

a biocompatible viscoelastic material filling said envelope in an amount sufficient to provide said predetermined shape, said biocompatible viscoelastic material being a sterile, non-pyrogenic solution selected from the group consisting of salt of chondroitin sulfate, salts of hyaluronate, polysaccharide, hydroxypropylmethylcellulose and mixtures of at least two of this group; and a bioactive substance admixed in said polymer for elution from said microporous structure of said envelope after implantation and contact of said surface with tissue in a human, and having a concentration and molecular weight selected to achieve a desired equilibrium between said envelope surface and said tissue proximate said envelope upon implant to control said elution of said bioactive substance.

2. The device of claim 1, wherein said envelope is selected from the group consisting of silicone, polyurethane, polyvinyl alcohol, polyethylene, polyesters, tetrafluoroethylene and polytetrafluroethylene, hydrogels, fluorosilicone and mixtures of at least two of this group.

3. The device of claim 1, wherein said bioactive substance is selected from the group consisting of heparin, prostacyclenes, steroids, ibuprofen, antimicrobials, antibiotics, tissue plasma activators, monoclonal antibodies, snake venom protein by products, antifibrosis agents, cyclosporine and mixtures of at least two of this group.

* * * * *